United States Patent [19]
Mougin et al.

[11] Patent Number: 5,997,819
[45] Date of Patent: Dec. 7, 1999

[54] FLUID SAMPLING DEVICE COMPRISING A THERMAL CONTROL VALVE

[75] Inventors: Pascal Mougin, Rueil-Malmaison; Philippe Ungerer, Créteil; Gérard Moracchini, Andilly, all of France

[73] Assignee: Institut Francais Du Petrole, Cedex, France

[21] Appl. No.: 09/094,634

[22] Filed: Jun. 15, 1998

[30] Foreign Application Priority Data

Jun. 17, 1997 [FR] France ................................. 97 07610

[51] Int. Cl.⁶ ...................................................... G01N 1/10
[52] U.S. Cl. ...................... 422/100; 422/103; 436/174; 436/180; 73/863.12
[58] Field of Search ............................ 422/100, 99, 103; 73/1.04, 86.12, 864.01; 436/179, 174, 180

[56] References Cited

U.S. PATENT DOCUMENTS

| | | | |
|---|---|---|---|
| 3,429,186 | 2/1969 | Price et al. ............................... | 73/421.5 |
| 4,259,867 | 4/1981 | Fondos et al. ........................... | 73/421.5 |
| 4,367,645 | 1/1983 | Froment ................................... | 73/23.1 |
| 4,576,918 | 3/1986 | Yeung ...................................... | 436/179 |
| 4,779,466 | 10/1988 | Ramsner et al. ...................... | 73/863.33 |
| 5,855,852 | 1/1999 | Bienhaus et al. ........................ | 422/102 |
| 5,879,635 | 3/1999 | Nason ...................................... | 422/102 |

FOREIGN PATENT DOCUMENTS

| | | |
|---|---|---|
| 3423200 | 1/1985 | Germany . |
| 3528924 | 10/1988 | Germany . |

*Primary Examiner*—Long V. Le
*Assistant Examiner*—Kathryn Bex
*Attorney, Agent, or Firm*—Antonelli, Terry, Stout & Kraus, LLP

[57] ABSTRACT

Fluid sampling device comprising a sampling cell provided with a thermal control valve consisting of a plug made from a solid low-melting temperature alloy that is made permeable to the fluid by heating the metal alloy to its melting temperature. The device mainly comprises an intermediate cell with a central channel provided with a plug made from a low-melting temperature alloy which fits into the inlet hole of the sampling cell. A connecting device for connecting the two cells together and an element which connects the intermediate cell via a fine linking tube to a reactor producing the fluid to be sampled.

5 Claims, 2 Drawing Sheets

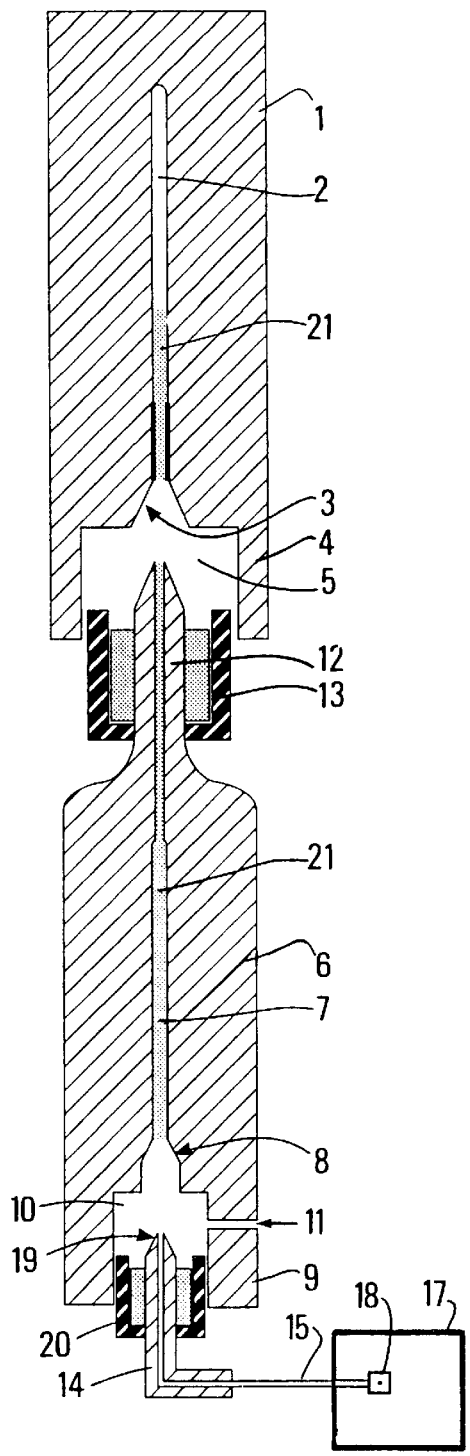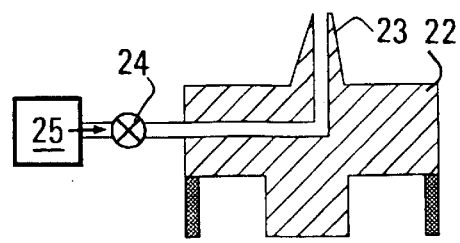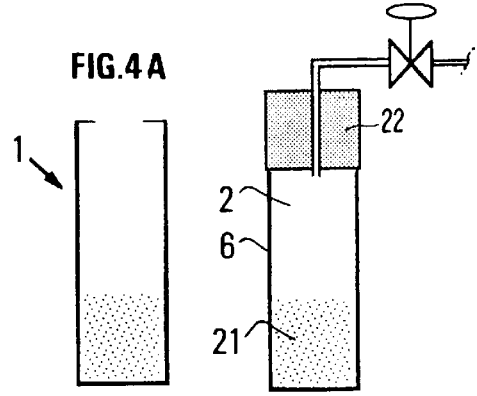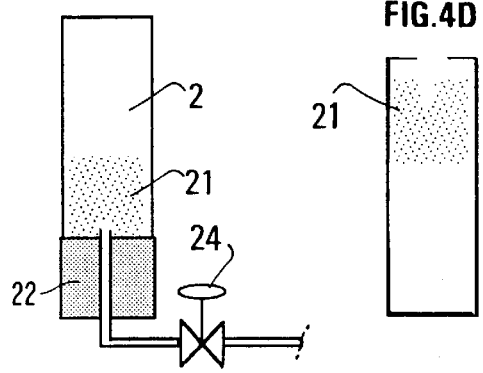

FIG.2

| Nom | % Sn | % Bi | % Pb | % Cd | Divers | Tf (°C) |
|---|---|---|---|---|---|---|
|  | 99,25 |  |  |  | 0,5 % Cu | 227 |
|  | 25,9 | 53,9 |  | 20,2 |  | 103 |
| Wood | 12,5 | 50 | 25 | 12,5 |  | 70 |
| Cerrolow | 8,3 | 44,7 | 22,6 | 5,3 | 19,1 % In | 47 |

FLUID SAMPLING DEVICE COMPRISING A THERMAL CONTROL VALVE

FIELD OF THE INVENTION

The present invention relates to a fluid sampling device comprising a thermal control valve.

The device lends itself to many applications where control of an evolutionary process or characterization of phase equilibria requires successive and distinct fluid samplings while reducing the effects of contamination due to dead volumes remaining in the sampling circuits.

BACKGROUND OF THE INVENTION

The sampling device according to the invention can be used for example to take fluid samples within the scope of oil or fluid pyrolyses in closed reactors. In order to be representative of the evolution of natural basins, these reactions last for several days or even several weeks. The kinetics of such reactions can be obtained according to two approaches.

The first approach, described for example by:

Ungerer P. et al, 1988, in Kinetic Modelling of Oil Cracking, Org. Geochem., 13, 857–868, consists in carrying out pyrolyses of increasing duration. At the end of each of the successive experiments, the kinetics is stopped by means of an abrupt temperature drop. The conversion coefficients and the reaction rates are thus acquired at different times.

The other approach consists in performing successive samplings during the progress of a single experiment. Considering the duration of pyrolysis reactions, this approach has the advantage of reducing the total acquisition time. The entire kinetics can be obtained with a single handling whereas the number of experiments should be multiplied with the first technique. The method of operation through sampling also allows to check that the reactive medium has always had the same (thermal and therefore reaction) history in time, which is not always the case when experiments are repeated. On the other hand, using successive samplings requires a greater reaction volume in order to make sure that the sum of the various aliquots extracted in the course of time will not lead to considerable changes in the operating conditions of the reaction system. The implementation difficulty of this approach at high pressures is due to the considerable dead volume inherent in conventional needle valves.

SUMMARY OF THE INVENTION

The fluid sampling device according to the invention, which comprises a sampling cell for collecting fluid, provided with an inlet hole, is characterized in that the sampling cell is insulated by a thermal control valve consisting of a plug made from a solid low-melting temperature material that is made permeable to the fluid by temporary heating.

According to a preferred embodiment, the plug that seals the inlet hole is made from a stable melting temperature eutectic metal alloy such as Wood's metal for example.

According to an embodiment, the device comprises an intermediate cell with a central channel provided with a plug made of said solid material, which communicates an inlet with a first end and an outlet with the opposite end thereof, and suited to tightly fit into the inlet hole of the sampling cell, a means for connecting the sampling cell to the intermediate cell, an element associated with seal means for connecting, at the inlet of the intermediate cell, a fine linking tube to a reactor producing the fluid to be sampled.

According to an embodiment suited for fluid sampling under elevated pressure, the sampling cell is provided with a fine inlet channel, the section and the length of this inlet channel and those of the central channel of the intermediate cell are so selected that the plugs formed by cooling of said material are sealed against the fluid sampled.

The method for implementing the device according to the invention comprises:

a sampling cell preparation stage comprising transfer of a certain volume of said material in the liquid state into said cell, suction of the fluid contained in the cell, transfer of said volume of material into the inlet of the cell and cooling thereof so as to form a sealed plug, and a sampling stage comprising communicating the sampling cell with a vessel containing the fluid to be sampled, and temporary heating of said plug (which leads to the melting thereof) in order to make it permeable to the fluid.

According to an embodiment, the method further comprises a stage of preparation of an intermediate cell in order to form therein a second solid plug made from said material, said sampling also comprising combined heating of the second plug in order to make it permeable to the fluid.

A capillary tube is preferably used to connect the reactor to the intermediate cell so as to minimize dead volumes.

Fluid ampoules are thus available for subsequent treatments. There is no constraint concerning the conservation thereof and this storage method allows high flexibility during later analyses. The consequence of certain sampling methods is the use of suited analysis techniques: in many fluid analysis cases specific chromatography injectors have to be used. The sampling mode described hereafter requires no adjustment of existing sensing devices and all of the conventional devices can be used.

A valve of this type has many advantages in comparison with conventional valves used in laboratory devices:

it is economical while providing perfect sealing. The installation thereof is much simpler than that of a conventional valve. The installation simplicity thereof combined with its low cost, makes it possible to manufacture sample ampoules that can optionally be expandable. A batch of ampoules containing fluid samples representative of successive times of a reaction spread over a relatively long period can be readily constituted and it is therefore possible to simplify the organization of the stage of acquisition and processing of data relative to this reaction, which can last for a shorter time.

The characteristics of this type of valve are well reproducible which facilitates comparisons between the successive fluid samples. It is also possible with this type of valve to reduce dead volumes to very little so that trails are negligible and the successive samples are entirely independent of one another.

Once the sampling performed, the sampling cell can be removed, the intermediate cell with its solidified "thermal valve" tightly insulating the reaction chamber, and a new fluid recovery cell can be set for a new sampling operation.

BRIEF DESCRIPTION OF THE DRAWINGS

Other features and advantages of the method according to the invention will be clear from reading the description hereafter of a non limitative example suited to the sampling of fluid samples under very elevated pressure, with reference to the accompanying drawings wherein:

FIG. 1 diagrammatically shows the device with its various parts in a semi-dislodged position, FIG. 2 is a table of various alloys, with their composition and their melting temperature, which can be used to form the thermal-effect valve used in the to present device, FIG. 3 shows an end plug used in the preparatory stage prior to sampling, and FIGS. 4a, 4b, 4c, 4d illustrate various operations required for preparation of a sampling cell.

DETAILED DESCRIPTION OF THE INVENTION

Sampling cell 1 comprises (FIG. 1) a fine central inlet channel 2 ending in a wide-necked end 3 and a tubular extension 4 whose section is larger than that of central channel 2, forming an inlet cavity 5.

Each fluid sample is taken by means of an intermediate cell 6 through which a fine longitudinal channel 7 runs. At a first end, fine channel 7 opens, through a wide-necked end 8, into a tubular extension 9 forming an inlet cavity 10. A leakage hole 11 is radially provided through the wall of tubular extension 9. At the opposite end, intermediate cell 6 is extended by a beveled beak 12 suited to closely fit, during operation, into the wide-necked end 3 of sampling cell 1 so as to establish a continuity between the channels 2 and 7 of cells 1 and 6. An annular seal connection 13 whose section is suited to that of inlet cavity 5 of sampling cell 1 is associated with beak 12.

The fluid to be transferred into intermediate cell 6 flows in through a joining element 14 in which a (0.2-mm inside diameter for example) capillary tube 15 connected to a high-pressure vessel (or cell) 17 containing the fluid to be sampled is inserted. A filter 18 made of sintered metal for example is placed at the inlet of the capillary tube (in vessel 17 for example) in order to hold back solid particles likely to be mixed with the fluid to be sampled. The other end of joining piece 14 ends in a point 19 suited to closely fit, during operation, into wide-necked end 8. An annular coupling 20 allows to provide a sealed connection between joining piece 14 and inlet cavity 10.

Closing of the fine channels 2 and 7 in cells 1 and 6 is provided by "thermal-effect valves", in this case plugs 21 made from a low-melting point substance whose characteristics are suited to the application required.

In the case of applications where gaseous samples are to be taken at very high pressures that may reach 100 MPa, a low-melting point metal in the solid form is preferably used to form these sealed "thermal locks" between the reactive medium (high-pressure cell 17) and the sampling zone (cells 1 and 6). During sampling, the solid metal is brought to the melting point thereof and the reactive fluid can then flow through the column of liquid metal and migrate to the sampling zone (sampling cell 1). Once the sample obtained, the metal is cooled, it solidifies and thus entraps the fluid.

The metal used in the device must have a sufficiently low melting point so that it can be reached quite rapidly. The liquid-solid change must occur at a given temperature. It is thus possible to use a pure substance or alloys, but the latter must have a eutectic structure.

As shown in FIG. 2, various types of eutectic alloys based on tin, bismuth, lead and cadmium can be selected, with different melting temperatures according to the proportions of the various metal constituents.

According to the temperature of the reaction medium and of the environment of the sampling system, it is advisable to take the highest possible temperature compatible with the sample stability, thus preventing accidental melting of the metal. For standard temperature applications, the metal known as Wood's metal, which is an alloy of bismuth, lead, tin and cadmium and which has a melting point of 70° C., is for example used.

One of the main interests of these alloys is that they expand as they cool down, especially in the case of high bismuth contents. In general, when the bismuth content is above 55%, the alloys expand, and if this content falls below 48%, they shrink. There is almost no volume variation between these two values. This is notably the case with Wood's metal whose volume remains stable as it cools down, which prevents any possibility of leakage of the fluid entrapped in the sampling cell.

The wall of cells 1 and 6 is of course more or less thick according to the pressure of the samples taken, and the volume thereof is also suited to that of the samples to be taken.

The assembly described above forms the sampling device. The implementation thereof also requires various plugs which will serve for introduction of the alloy and possibly in case of a fluid leakage. All of these blocking elements comprise (FIG. 3) a first plug 22 suited to the inlet cavity 5 of the sampling cell, also provided with a beak 23 intended to come into contact with the bottom of wide-necked part 3. The plug is crossed by a bent channel opening into the point of beak 23, allowing to communicate the central channel 2 of sampling cell 1 with an evacuating means 25 by means of a valve 24 as explained hereunder.

Preparation of the Sampling Device

A stage of preparation of cells 1 and 6 is performed prior to the sampling operations.

The opening at the end of beak 12 at one end of intermediate cell 6 is closed and the central channel (as shown in FIG. 1) is filled with metal brought to the melting point thereof. Rather slow cooling allows a high-grade metallic plug to form while avoiding mechanical stresses.

The sampling cell is prepared as follows. The opening thereof being directed upwards, a volume of liquefied metal is poured therein while hot (FIG. 4a) and it accumulates on the bottom. The cell opening is thereafter covered with the plug of FIG. 3 and it is communicated through the opening of valve 24 with a water pump (not shown) so as to evacuate it (FIG. 4b). Valve 24 being closed, cell 1 is turned upside down and the entire cell is brought to the melting temperature so that the metal accumulates at the base (FIG. 4c). The metal thereafter just has to be cooled to solidify and the sampling cell is thus sealed after plug 22 has been removed (FIG. 4d).

Assembly of the Device

The device is assembled as follows a) capillary tube 15 is first connected to reaction cell 17, b) bent pipe 14 associated with coupling 20 is fitted into housing 8, 10 at the base of intermediate cell 6 so as to establish a continuity between beveled point 19 and central channel 7 closed by metallic plug 21, and c) upper beak 12 and its associated connection 13 are similarly fitted into housing 3, 5 also in order to establish a continuity between the metallic plugs of cells 1, 6.

Sampling

It is performed as follows:

Intermediate cell 6 and sampling cell 1 are brought to the melting temperature. The metal melts in channels 2 and 7, which makes it permeable to the fluid under pressure from reactor 17. The fluid rises through the column of liquefied metal and accumulates in the sampling cell.

When sampling is completed, the metal is progressively cooled from the end of capillary tube 15 that is the closest to reactor 17 up to sampling cell 1 so that the metallic plug which forms again is perfectly sealed.

Connection 13 then just has to be dismantled and the metallic bond that may now have formed just has to be broken to release sampling cell 1. Reaction chamber 17 is insulated by the cooled "thermal valve" of intermediate cell 6. The reaction kinetics can be stopped by quenching.

A new sampling cell 1 can then be coupled to intermediate cell 6 in order to perform a new sampling operation.

Using a capillary tube 15 allows to reduce the sampling volume. No draining is performed, the fluid present in the capillary tube, which has a thermal history that is different from that of the fluid in the reactor, is recovered but the volume thereof is negligible in relation to the sampled volume.

Sampling Device Dimensioning Methodology

Dimensioning of the device requires defining the minimum diameter of the tubes that are to be filled with metal. The required height of the metal plug which serves as a seal for the system under the pressure considered also has to be determined.

Preliminary experiments with variable diameter tubes must therefore be carried out in order to determine the minimum diameter so as to ensure passage of the fluid through columns of molten metal of different diameters because, if the diameter is too small, the capillary forces prevent ascent of the fluid drops or bubbles.

Once the diameter is selected, the height of metal required for the maximum pressure of the reactor has to be determined. This parameter can be estimated by means of numerical mechanical resistance simulations and checked by means of tests.

Variants

Without departing from the scope of the invention, it is also possible to use, for other applications where the pressures are much lower, a thermal valve using other materials than the alloys mentioned by way of example, or a sampling cell of any shape with a differently dimensioned inlet that can receive fluid samples without requiring an intermediate cell.

We claim:

1. A fluid sampling device comprising a sampling cell (1) for collecting a fluid, provided with an inlet hole, characterized in that the sampling cell (1) is insulated by a thermal control valve consisting of a plug (21) positioned in the inlet hole for sealing said inlet hole where said plug is made from a solid low-melting temperature material which is made permeable to the fluid by temporary heating said material to its melting temperature.

2. A device as claimed in claim 1, characterized in that the plug (21) is made from a stable melting temperature eutectic metal alloy.

3. A device as claimed in claim 2, characterized in that the metal alloy is Wood's metal.

4. A device as claimed in claim 1, further comprising an intermediate cell (6) with a central channel (7) provided with a plug (21) made from said solid material, which communicates an inlet (8, 10) to a first end and an outlet (12) to the opposite end, and suited to fit into the inlet hole (3, 5) of the sampling cell (1), a means (13) for connecting the sampling cell to the intermediate cell (6), an element (14) associated with seal means (20) for connecting, at the inlet (8, 10) of the intermediate cell (6), a fine linking tube to a reactor (17) producing the fluid to be sampled.

5. A device as claimed in claim 4, wherein said fluid being under elevated pressure and, characterized in that the sampling cell is provided with a fine inlet channel (2), a section and length of the inlet channel (2) and those of central channel (7) of intermediate cell (6) being so selected that the plug (21) formed by cooling of said material is sealed against the fluid sampled.

\* \* \* \* \*